United States Patent
Davis

(10) Patent No.: US 11,903,902 B2
(45) Date of Patent: Feb. 20, 2024

(54) FLUID TRANSFER COUPLINGS

(71) Applicant: Benjamin Martin Davis, Woodstock, GA (US)

(72) Inventor: Benjamin Martin Davis, Woodstock, GA (US)

( * ) Notice: Subject to any disclaimer, the term of this patent is extended or adjusted under 35 U.S.C. 154(b) by 0 days.

(21) Appl. No.: 18/092,235

(22) Filed: Dec. 31, 2022

(65) Prior Publication Data

US 2023/0211140 A1 Jul. 6, 2023

Related U.S. Application Data

(60) Provisional application No. 63/296,004, filed on Jan. 3, 2022.

(51) Int. Cl.
| | | |
|---|---|---|
| *A61J 1/20* | (2006.01) | |
| *A61J 1/14* | (2023.01) | |
| *A61M 39/10* | (2006.01) | |

(52) U.S. Cl.
CPC .......... *A61J 1/2089* (2013.01); *A61J 1/1412* (2013.01); *A61J 1/2058* (2015.05); *A61J 1/2065* (2015.05); *A61J 1/2096* (2013.01); *A61M 39/10* (2013.01); *A61J 1/1418* (2015.05); *A61M 2039/1077* (2013.01)

(58) Field of Classification Search
CPC ...... A61J 1/2058; A61J 1/2065; A61J 1/2096; A61J 1/1418
See application file for complete search history.

(56) References Cited

U.S. PATENT DOCUMENTS

| | | |
|---|---|---|
| 2,290,348 A | 7/1942 | Moule |
| 2,434,612 A | 1/1948 | Hamiel |
| 2,783,908 A | 3/1957 | Winfield |
| 3,307,752 A | 3/1967 | Anderson |
| 3,545,637 A | 12/1970 | Barr |
| 3,645,262 A | 2/1972 | Harrigan |
| 3,735,888 A | 5/1973 | Jacko |
| 4,230,112 A | 10/1980 | Smith |
| 4,303,071 A | 12/1981 | Smith |
| 4,317,448 A | 3/1982 | Smith |
| 4,493,348 A | 1/1985 | Lemmons |
| 4,508,236 A | 4/1985 | Keilman et al. |
| 4,515,752 A | 5/1985 | Miramanda |

(Continued)

FOREIGN PATENT DOCUMENTS

| | | |
|---|---|---|
| CN | 112208932 A | 1/2021 |
| DE | 20302788 U1 | 6/2004 |

(Continued)

OTHER PUBLICATIONS

Baxa Adapta-Cap Bottle Adapter; 1 pg; date unknown.

(Continued)

*Primary Examiner* — Leslie R Deak
(74) *Attorney, Agent, or Firm* — Perilla Knox & Hildebrandt LLP

(57) ABSTRACT

Fluid transfer couplings or connectors including dual function press-in bottle adaptors supporting different syringe types, connectors having a universal port for supporting different syringe types, transfer couplings compatible for use with different syringe types. Other caps and closures incorporating couplings for fluid transfer with different syringe types is also disclosed.

20 Claims, 14 Drawing Sheets

(56) References Cited

U.S. PATENT DOCUMENTS

| | | |
|---|---|---|
| 4,573,506 A | 3/1986 | Paoletti |
| 4,685,173 A | 8/1987 | Pavur |
| 4,883,483 A | 11/1989 | Lindmayer |
| 4,944,736 A | 7/1990 | Holtz |
| 5,060,812 A | 10/1991 | Ogle, II |
| 5,088,612 A | 2/1992 | Storar et al. |
| 5,232,109 A | 8/1993 | Tirrell et al. |
| 5,238,130 A | 8/1993 | Marques et al. |
| 5,356,406 A | 10/1994 | Schraga |
| 5,429,256 A | 7/1995 | Kestenbaum |
| 5,454,409 A | 10/1995 | McAffer et al. |
| 5,454,805 A | 10/1995 | Brony |
| 5,484,070 A | 1/1996 | Graham |
| 5,573,525 A | 11/1996 | Watson et al. |
| 5,598,939 A | 2/1997 | Watson et al. |
| 5,620,434 A | 4/1997 | Brony |
| 5,688,254 A | 11/1997 | Lopez et al. |
| D398,060 S | 9/1998 | Brown |
| 5,902,298 A | 5/1999 | Niedospial, Jr. et al. |
| 5,921,419 A | 7/1999 | Niedospial, Jr. et al. |
| 5,931,828 A | 8/1999 | Durkee |
| 5,971,181 A | 10/1999 | Niedospial, Jr. et al. |
| 6,056,135 A | 5/2000 | Widman |
| D528,910 S | 9/2006 | Kingsley |
| D530,200 S | 10/2006 | Kingsley |
| 7,128,228 B2 | 10/2006 | Collins |
| 7,681,750 B2 | 3/2010 | Jäckel |
| 7,717,281 B2 | 5/2010 | Baudin |
| D627,899 S | 11/2010 | Cofie |
| 7,832,581 B2 | 11/2010 | Van Cromvoirt |
| D630,732 S | 1/2011 | Lev et al. |
| 7,985,205 B2 | 7/2011 | Adams |
| D644,618 S | 9/2011 | Morihira |
| 8,100,854 B2 | 1/2012 | Vögelin et al. |
| D674,277 S | 1/2013 | Hanson et al. |
| 8,459,312 B2 | 6/2013 | Manera et al. |
| 8,464,882 B2 | 6/2013 | Tirosh |
| D686,339 S | 7/2013 | Shima et al. |
| 8,551,068 B2 | 10/2013 | Kyle et al. |
| D693,923 S | 11/2013 | Hernandez et al. |
| D706,135 S | 6/2014 | Hutchison |
| 8,758,322 B2 | 6/2014 | McCoy et al. |
| D714,142 S | 9/2014 | Hojo |
| D716,636 S | 11/2014 | McDonald |
| D723,181 S | 2/2015 | Kawamura |
| 8,950,608 B2 | 2/2015 | Dejong |
| D725,284 S | 3/2015 | Karlsson et al. |
| 8,967,405 B2 | 3/2015 | Morrone |
| D731,065 S | 6/2015 | Winter |
| D737,962 S | 9/2015 | Schultz |
| 9,126,029 B2 | 9/2015 | Fangrow et al. |
| 9,156,569 B2 | 10/2015 | Vassallo et al. |
| 9,296,531 B2 | 3/2016 | Luzbetak et al. |
| D756,200 S | 5/2016 | McDonald |
| 9,345,639 B2 | 5/2016 | Ferrara |
| 9,433,562 B2 | 9/2016 | Ingram et al. |
| 10,058,481 B1 * | 8/2018 | Russo .............. A61J 1/1481 |
| 10,857,068 B2 | 12/2020 | Davis et al. |
| 11,166,876 B2 | 11/2021 | Davis et al. |
| 2005/0258125 A1 | 11/2005 | Kiehne |
| 2006/0217679 A1 | 9/2006 | Hanly et al. |
| 2008/0015539 A1 * | 1/2008 | Pieroni ............. A61J 1/2096 604/403 |
| 2009/0230075 A1 | 9/2009 | Springer |
| 2009/0321611 A1 | 12/2009 | Moberg |
| 2010/0327010 A1 * | 12/2010 | Manera ............ B65D 47/2031 141/357 |
| 2011/0054436 A1 | 3/2011 | Griffis, III et al. |
| 2012/0103470 A1 | 5/2012 | Terwilliger |
| 2012/0104054 A1 | 5/2012 | Terwilliger |
| 2012/0216909 A1 | 8/2012 | Levy |
| 2012/0289936 A1 | 11/2012 | Ingram et al. |
| 2014/0246616 A1 | 9/2014 | Fangrow |
| 2014/0299568 A1 | 10/2014 | Browne |
| 2015/0126941 A1 | 5/2015 | Felts et al. |
| 2015/0129535 A1 | 5/2015 | Morrone, III |
| 2015/0238387 A1 | 8/2015 | Caetano |
| 2015/0320638 A1 | 11/2015 | Becker et al. |
| 2016/0015601 A1 | 1/2016 | Davidson |
| 2016/0067147 A1 | 3/2016 | Davis et al. |
| 2016/0159635 A1 | 6/2016 | Davis et al. |
| 2016/0217679 A1 | 7/2016 | McNutt et al. |
| 2016/0317393 A1 | 11/2016 | Davis et al. |
| 2016/0367439 A1 | 12/2016 | Davis et al. |
| 2017/0014616 A1 | 1/2017 | Davis et al. |
| 2017/0239141 A1 | 8/2017 | Davis et al. |
| 2018/0099791 A1 | 4/2018 | Doornbos et al. |
| 2019/0105484 A1 * | 4/2019 | Doornbos .......... A61J 15/0026 |

FOREIGN PATENT DOCUMENTS

| | | |
|---|---|---|
| EP | 0960616 A2 | 12/1999 |
| EP | 2959877 A1 | 12/2015 |
| GB | 2379253 A | 3/2003 |
| TW | M512003 U | 11/2015 |
| WO | 1998003210 A2 | 1/1998 |
| WO | 1998046278 A1 | 10/1998 |
| WO | 1999032155 A2 | 7/1999 |
| WO | 2002085429 A2 | 10/2002 |
| WO | 2005065767 A2 | 7/2005 |
| WO | 2005087127 A1 | 9/2005 |
| WO | 2009068987 A1 | 6/2009 |
| WO | 2012024370 A1 | 2/2012 |
| WO | 2013081699 A2 | 6/2013 |
| WO | 2014077670 A1 | 5/2014 |
| WO | 2015146831 A1 | 10/2015 |
| WO | 2016040126 A1 | 3/2016 |
| WO | 2016089869 A1 | 6/2016 |
| WO | 2018022631 A1 | 2/2018 |

OTHER PUBLICATIONS

Baxa (Baxter) RAPIDFILL Connector; 1 pg; date unknown.
Baxter AdaptACap Bottle Adapter; 1 pg; date unknown.
BioJect Needle-Free Vial Adapter; 1 pg; date unknown.
CareFusion Universal Vented Vial Adapter; 2 pgs; 2013.
Iso-Med Press-In Bottle Adapters; 1 pg; date unknown.
Medela Breastmilk Transfer Lid; 1 pg; date unknown.
Medicina ENFit Press in Adapter; 18 pgs; date unknown.
Medi-Dose EPS Press-In Bottle Adapters; 1 pg; date unknown.
Medispense Stepped Stopper; 1 pg; date unknown.
NeoMed Closed System NeoBottle; 1 pg; date unknown.
Non Sterile Luer Lock to Oral Slip Adapter; Health Care Logistics, Inc.; 1 pg; date unknown.
Oral Slip to Oral Slip Adapter; Health Care Logistics, Inc.; 1 pg; date unknown.
PDG—The Packaging Design Group Sealsafe Press in Bottle Adapter (PIBA); 1 pg; date unknown.
Specialty Medical Products Coupling (Item Code SMP-SCFF); Apr. 10, 2014; 1 pg.
Sterile Luer Lock to Oral Slip Adapter; Health Care Logistics, Inc.; 1 pg; date unknown.
Total Pharmacy Supply Bottle Adapter Plug; 1 pg; date unknown.
Total Pharmacy Supply Universal Bottle Adapter; 1 pg; date unknown.
WestPharma Vial Adapters; 2 pgs; 2014.
Vygon Fluid Dispensing Connector; 1 pg; date unknown.
Comar Oral Syringe Bottle Adapters; 3 pgs; date unknown.
GEDSA ENFit Pharmacy Resource Guide; 3 pgs; date unknown.
The Oley Foundation Resource Guide; 4 pgs; date unknown.

\* cited by examiner

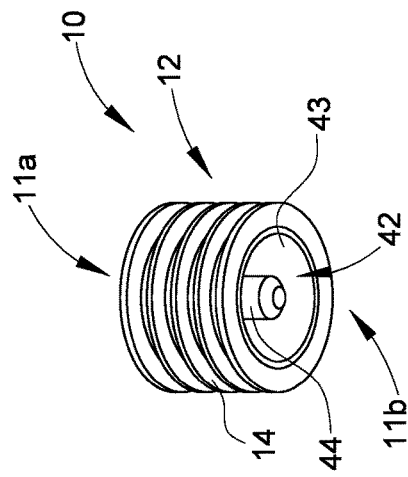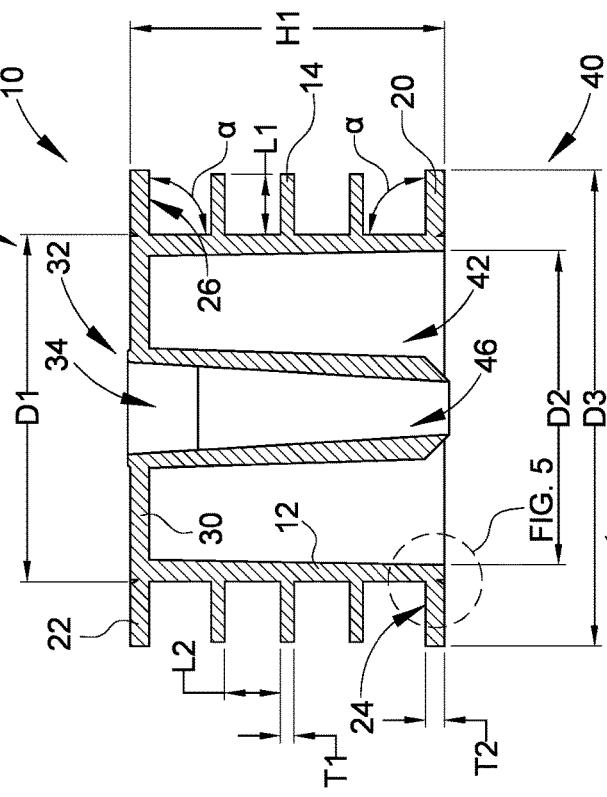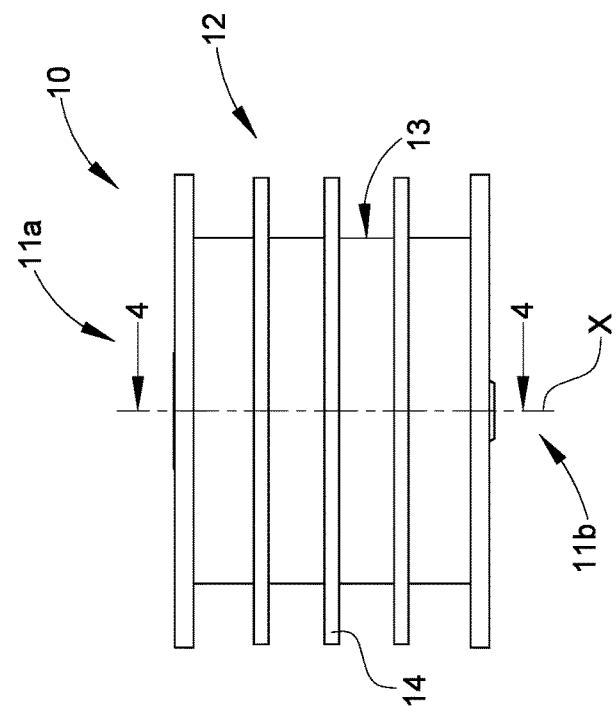

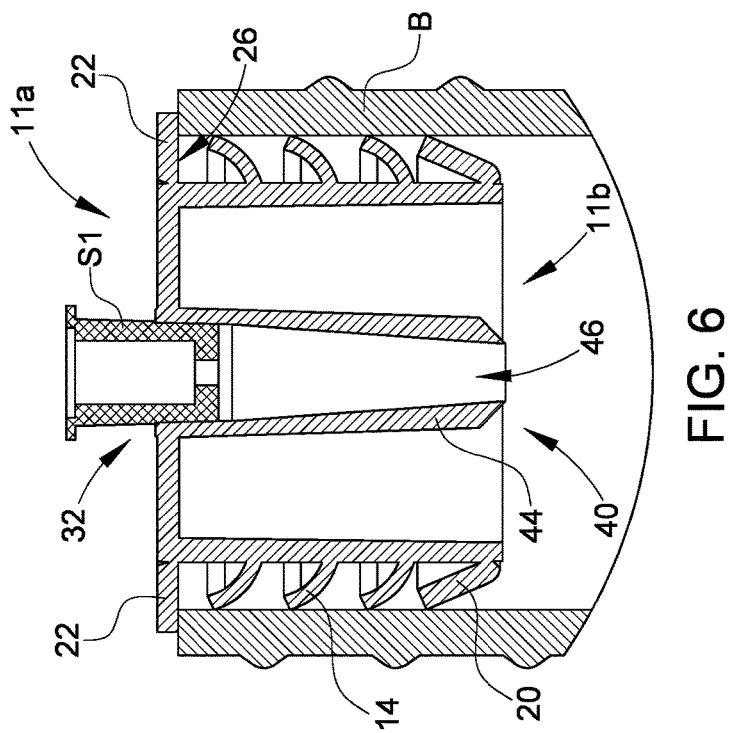
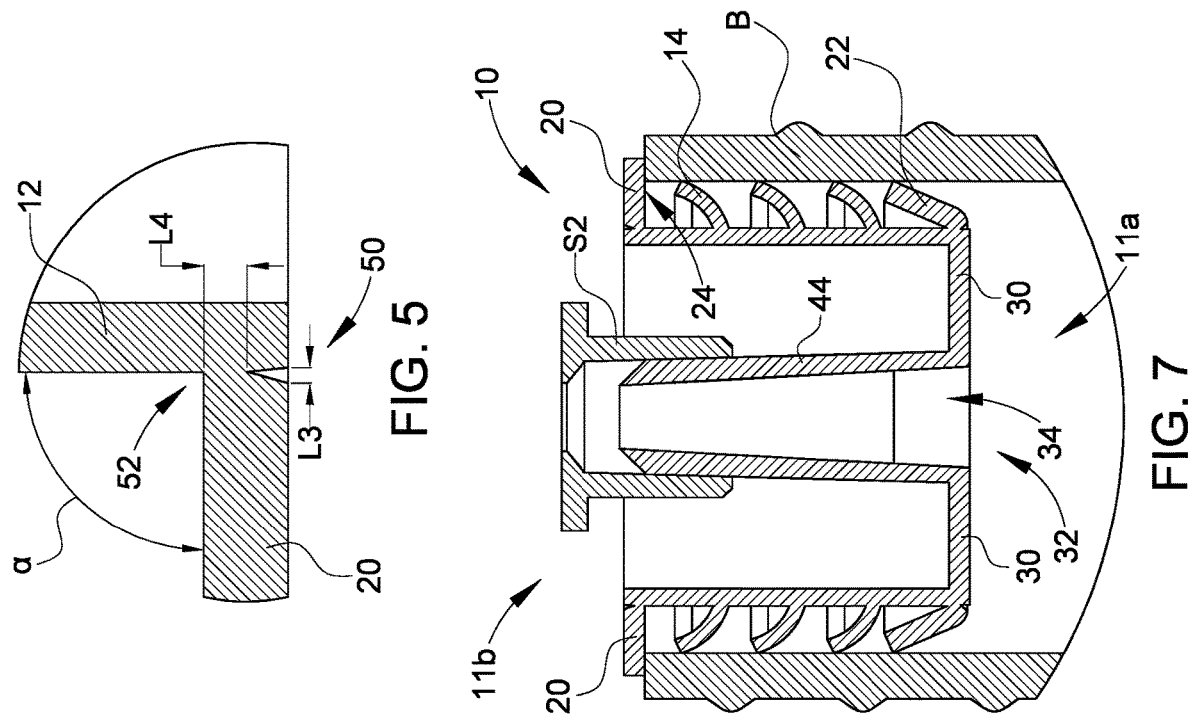

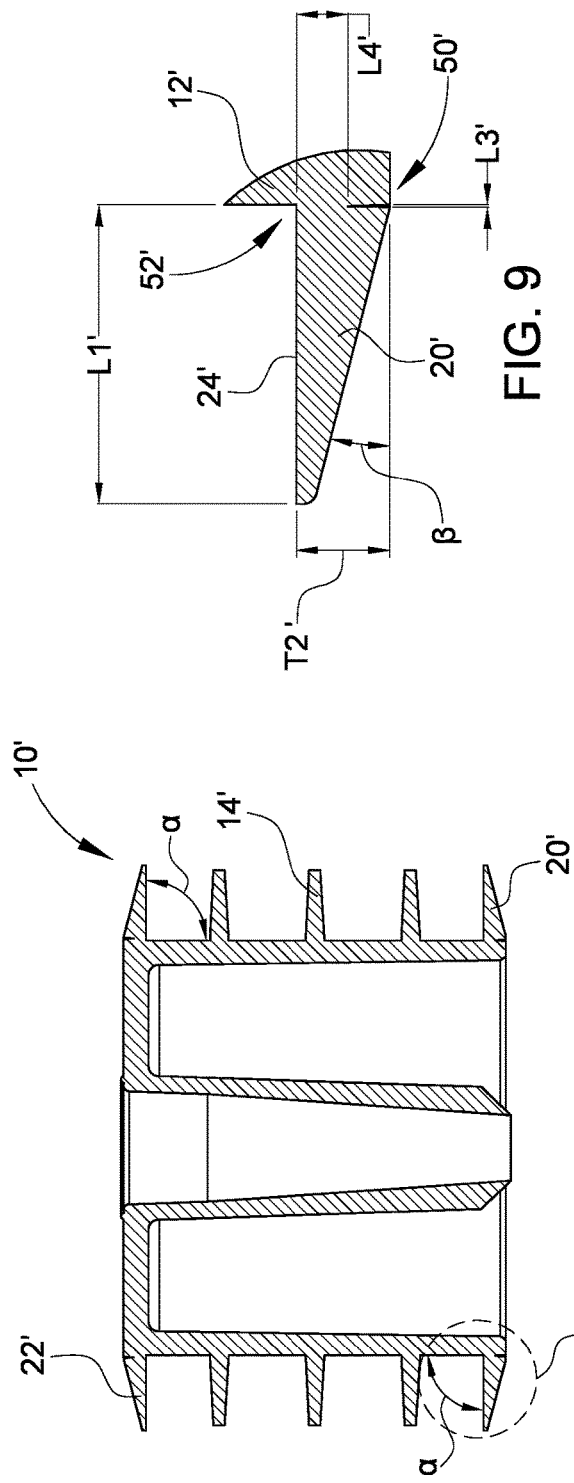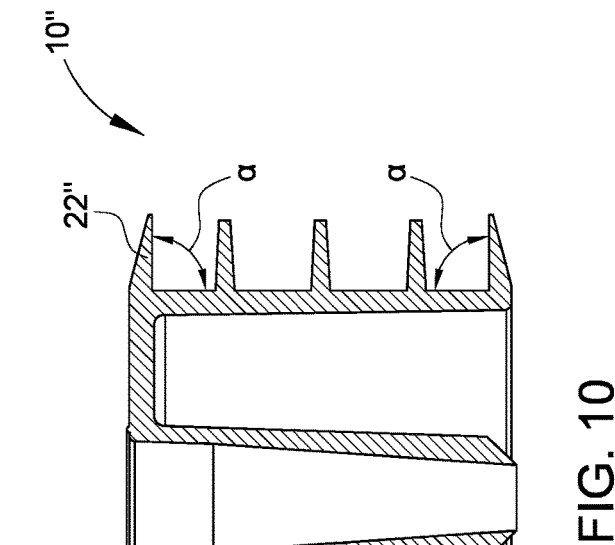
FIG. 9
FIG. 10
FIG. 8

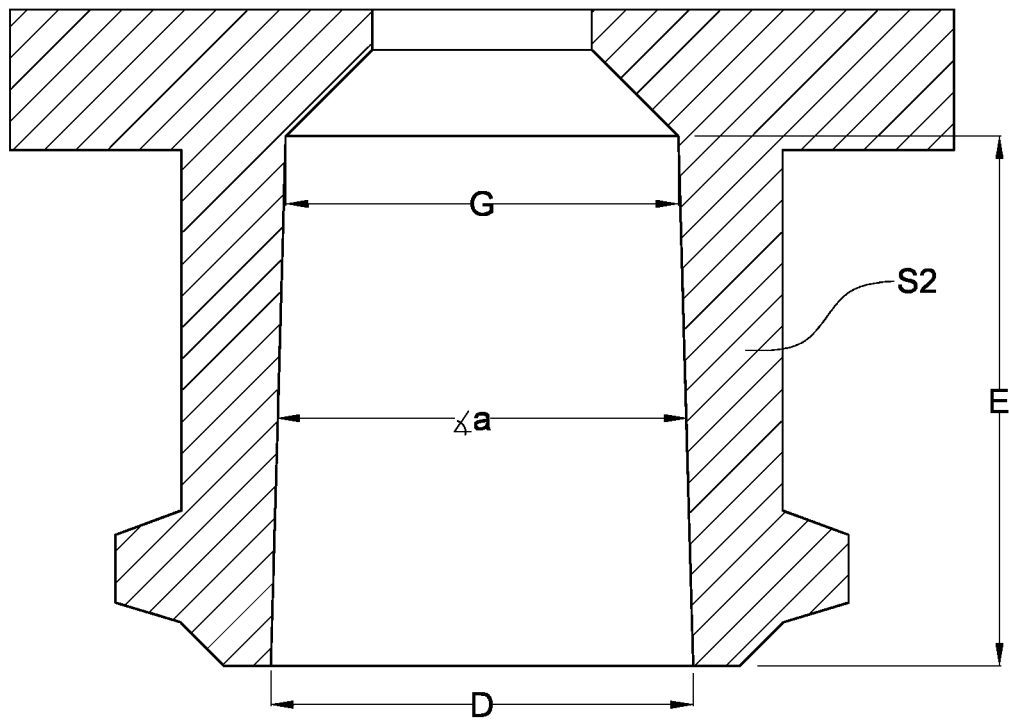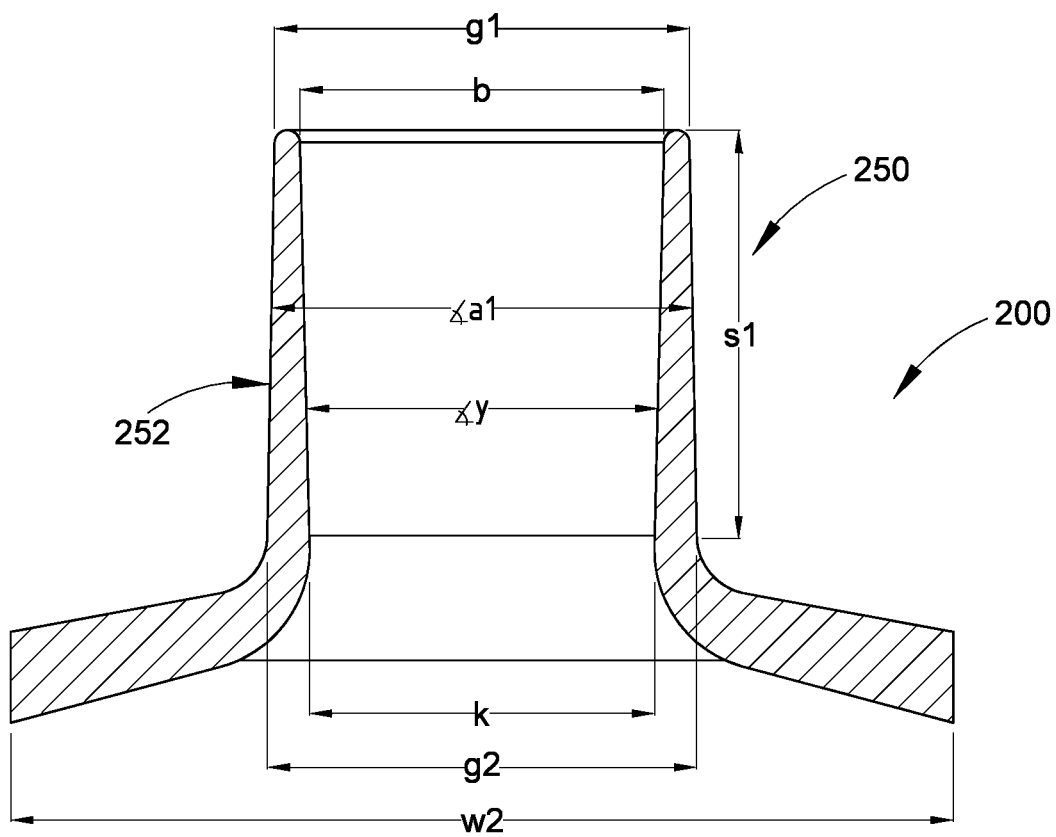
FIG. 19

FLUID TRANSFER COUPLINGS

CROSS REFERENCE TO RELATED APPLICATION

The present application claims priority to U.S. Provisional Patent Application No. 63/296,004 filed Jan. 3, 2022, the entirety of which is incorporated by reference herein.

TECHNICAL FIELD

The present invention relates generally to the field of child resistant medication bottle caps, drug delivery systems, medicine bottle syringe adapters, and pharmacy accessories that facilitate the transfer of fluids.

BACKGROUND

Various containers are used for the collection, storage, dispensing and delivery of fluids such as medications, supplements, breast milk, formula and the like. Many oral medications that are used with children come in a liquid form so that they are easier for a child to take, as opposed to swallowing the pill form of the medication. These liquid medications are often provided in medication bottles and they are often administered with an oral and or enteral syringe. These syringes are used because they provide the easiest and most accurate method for withdrawing and then administering the medication. However, medication bottles are typically offered with only a child resistant cap and often an adapter or separate cap is needed to facilitate connection with a syringe. These adapters and caps that are meant to facilitate connection with a syringe often do not have child resistant features and or they may compromise the child resistant functionality when used in conjunction with a child resistant medication bottle cap. Existing medicine bottle syringe adapters also only allow for one type of syringe connection. This is problematic because there are two different prevalent styles of enteral/oral syringes on the market and they have different tips/connectors. These are male oral slip tip syringes and ISO 80369-3 (commonly called ENFit®) compliant syringes.

It is to the provision of fluid transfer couplings meeting these and other needs that the present invention is primarily directed.

SUMMARY

In example embodiments, the present invention provides fluid transfer couplings. In example embodiments, the present invention provides dual connection capability for different syringe types to be able to connect and transfer fluids to and from medication bottles. In other embodiments, the present invention provides singular connection ports for either ISO 80369-3 compatible syringes or male orientated oral slip tip syringes to connect to. In example embodiments, the present invention is implemented in such ways as to offer the child resistant functionality that is common to medication bottle caps.

In one aspect, the present invention relates to a medicine bottle adapter including a cylindrical body extending between a first end and a second end, a hinged shelf provided at the ends of the cylindrical body, and one or more flanges along the cylindrical body between the hinged shelf of the first and second ends.

In example embodiments, the first end includes a female port configured for connection to a male oriented oral slip tip syringe. In example embodiments, the second end includes a male port configured for connection with an ISO 80369-3 compliant female tip syringe. In example embodiments, a radial cutout may be formed along the ends of the cylindrical body proximal their intersection with each hinged shelf. In example embodiments, a living hinge may be formed between each hinged shelf and the cylindrical body. In example embodiments, each hinged shelf is configured to permit inward pivoting thereof towards the cylindrical body yet resist pivoting thereof in an opposite direction away from the cylindrical body.

In example embodiments, the first end includes a first hinge flange and a first coupling and the second end includes a second hinge flange and a second coupling, wherein when the second coupling is to be used for fluid transfer, the first hinge flange is configured to pivot inwardly towards the cylindrical body and the second hinge flange is configured for acting as a stop against an end of an opening of the medicine bottle, and wherein when the first coupling is to be used for fluid transfer, the second hinge flange is configured to pivot inwardly towards the cylindrical body and the second hinge flange is configured for acting as a stop against the end of the opening of the medicine bottle. In example embodiments, the hinge flange of each end of the connector is configured for dual functionality. In example embodiments, the first coupling includes a female port configured for connection a male oriented oral slip tip syringe. In example embodiments, the second coupling includes a male port configured for connection with an ISO 80369-3 compliant female tip syringe.

In another aspect, the present invention relates to a child resistant medicine bottle cap including an inner threaded portion, an outer portion selectively engageable with the inner threaded portion, and a port connected with and extending through the inner threaded portion.

In example embodiments, the port is configured for connection with a male orientated oral slip tip syringe, an ISO 80369-3 compliant female tip syringe, or both. In example embodiments, the port can be positioned below, flush or above an outermost surface of the outer portion of the cap. In example embodiments, further includes a tethered cap or plug. In example embodiments, the bottle cap further includes a membrane having a slitted portion, wherein the slitted portion provides select access to a port positioned therebelow, the port configured for connection with a male orientated oral slip tip syringe or an ISO 80369-3 compliant female tip syringe.

In yet another aspect, the present invention relates to a fluid transfer connector including a male post comprising an outer surface, an inner surface, and a conduit extending therethrough, the male post being configured for sealing engagement with syringes of different formats, wherein a first syringe is configured for sealing engagement with the inner surface and wherein a second syringe is configured for sealing engagement with the outer surface.

In example embodiments, the first syringe comprises a male orientated oral slip tip syringe, and wherein an outer surface of the male tip sealingly engages with the inner surface of the male post. In example embodiments, the second syringe includes an ISO 80369-3 compliant female tip syringe, and wherein an inner surface of the female tip sealingly engages with the outer surface of the male post. In example embodiments, the connector is configured for attachment to a threaded opening of a bottle. In example embodiments, the connector is configured for attachment to an internal portion of a threaded opening of a bottle.

In yet another aspect, the present invention relates to a child resistant medicine bottle cap that contains a port for connection with a syringe that allows for fluid transfer to and from the bottle, while not compromising the child resistant feature of the cap. In one example embodiment, the port accepts a male orientated syringe. In another example embodiment, the port accepts a female orientated syringe. Other embodiments feature different configurations of these ports and combinations such that either a male or female orientated syringe may be used with the same cap or coupler to access the bottle.

These and other aspects, features and advantages of the invention will be understood with reference to the drawing figures and detailed description herein and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

FIG. 1 shows a first perspective view of a coupling according to an example embodiment of the present invention.

FIG. 2 shows a second perspective view of the coupling of FIG. 1 according to an example embodiment of the present invention.

FIG. 3 shows a side plan view of the coupling of FIG. 1.

FIG. 4 shows a cross-sectional view of the coupling of FIG. 3 taken along line 4-4.

FIG. 5 shows a detailed view of a portion of the coupling of FIG. 4.

FIG. 6 shows a cross-sectional view of the coupling of FIG. 1 fully inserted within an opening of a bottle in a first configuration, and showing a first syringe connected to a port thereof.

FIG. 7 shows a cross-sectional view of the coupling of FIG. 1 fully inserted within an opening of a bottle in a second configuration, and showing a second syringe connected to a port thereof.

FIG. 8 shows a cross-sectional view of a coupling according to another example embodiment of the present invention.

FIG. 9 shows a detailed view of a portion of the coupling of FIG. 8.

FIG. 10 shows a cross-sectional view of a coupling according to another example embodiment of the present invention.

FIG. 19 shows a cross-sectional view of FIG. 17.

DETAILED DESCRIPTION OF EXAMPLE EMBODIMENTS

Figure 11:
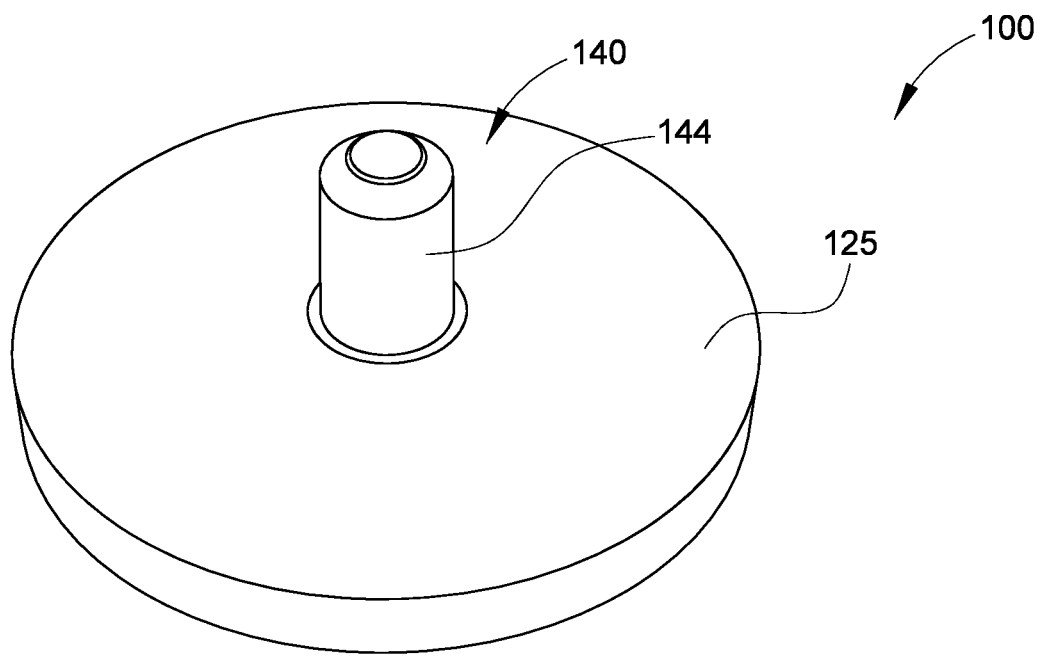
FIG. 11 shows a first perspective view of a coupling according to another example embodiment of the present invention.

The present invention may be understood more readily by reference to the following technical description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Example embodiments of the present invention comprise one or more configurations of child resistant caps, medicine bottle syringe adapters and couplers that feature an access port, or dual ports, for connection with syringes of different types such as ISO 80369-3 compatible syringes or male orientated oral slip tip syringes.

Other example embodiments herein provide for a plurality of couplers or adapters that feature one or more access ports that can be utilized with both types of syringes. According to some example embodiments, the present invention comprises a multi-functional or multi-syringe press-in bottle adaptor. According to some example embodiments, the present invention comprises medicine bottle caps that feature one or more access ports for connection with syringes for the means of fluid transfer, while still providing for the child resistant, typically described as a "push down and turn to open", feature that is common to medication bottle caps.

Preferably, the connectors, couplings or ports described herein do not form a seal with a Luer syringe (indicated for intravenous use). This is best practice because oral medications can cause severe injury or death if they are drawn up with IV/Luer syringes and then inadvertently administered intravenously.

With reference now to the drawing figures, wherein like reference numbers represent corresponding parts throughout the several views, FIGS. 1-10 show several example embodiments of a bottle adapter, coupler or connector 10. According to one example embodiment of the present invention and as depicted in FIGS. 1-7, the connector 10 comprises a cylindrical body 12 extending between a first end 11a and a second end 11b along an elongate axis X.

The cylindrical body 12 may comprise an outer peripheral surface 13 defining a plurality of spaced-apart flanges or steps 14 projecting outwardly therefrom, which are preferably flexible, resilient and sized to engage with bottle openings of a desirable size, extending around the entirety of the cylindrical body to define a continuous flange for providing frictional and sealing engagement with an internal surface or opening of the bottle B. In example embodiments, the bottle connector 10 is in the form of a "press-in" adapter, for example, such that the flanges or steps 14 along the outer peripheral surface 13 generally frictionally engage the opening of a bottle, for example, the opening of a pharmacy or medicine bottle B (see FIGS. 6-7). In example forms, commonly used bottles most frequently used in medicine practice range between about 1-16 ounces, and the opening thereof will generally vary according to its volume. In example embodiments, the connector 10 can be sized as desired, but can at least be provided in sizes compatible with bottle sizes (and the openings thereof) most frequently used in medicine practice, for example, between a diameter $D_1$ of about 9-47 millimeters, for example between about 10-39 millimeters according to one example embodiment. In some example embodiments, the bottle opening or inner diameter thereof is generally between about 10-45 millimeters.

According to example embodiments, the connector 10 comprises a hinged shelve 20, 22 at each respective end 11a, 11b of the cylindrical body 12. Accordingly, in comparison to prior "press-in" bottle connectors where only one orientation of the connector 10 can permit engagement with the opening of the bottle B, the connector 10 of the present invention is insertable within the opening of a bottle B in either a first orientation or a second orientation, for example, so as to provide for dual connection capability for different syringe types (for example, ISO 80369-3 compatible syringes or male orientated oral slip tip syringes).

In example embodiments, the flanges 14 comprise a thickness T1 and generally extend a length L1 outwardly from the outer peripheral surface 13, and the flanges 14 are generally laterally offset or spaced apart to define a length L2 therebetween. According to example embodiments, the thickness T1 is between about 0.125-1 millimeter, more preferably about 0.54 millimeters according to one example embodiment, the length L1 is between about 1-5 millimeters, more preferably about 2.8 millimeters according to one example embodiment, and the length L2 is between about 1.5-6 millimeters, more preferably about 3.41 millimeters according to one example embodiment. In example embodiments, the shelves 20, 22 comprise a thickness T2 and extend outwardly from the cylindrical body 12 to define an outer diameter D3. In example embodiments, the thickness T2 is generally between about 0.35-1.75 millimeters, for example, about 1 millimeter according to one example embodiment. The outer diameter D3 is generally sized to be generally similar to the outer diameter of the opening of the bottle B. According to one example embodiment, the outer diameter D3 is generally between about 12-45 millimeters. According to one example embodiment, the outer diameter D3 is about 21 millimeters. According to another example embodiment, the outer diameter D3 is about 24 millimeters.

In example embodiments, the hinged shelves 20, 22 may be configured for dual functionality, for example, permitting the shelves to serve as both a stop for engagement with the end of the bottle B opening (see stop surfaces 24, 26), or for example to serve as a flange or step when orienting the connector another way, for example, by inserting the connector within the opening of the bottle B, causing the shelf to hingedly fold or pivot about a living hinge 52 (see FIG. 5) towards the cylindrical body 12 aiding the lead in and reducing the insertion force required by the user (as opposed to fixed flanges), while its distal end is simultaneously engaging the interior surface of the open end of the bottle B, just as if it were a flange 14. According to example embodiments, the flange/shelf profile of the connector 10 may be substantially uniform wherein each end 11a, 11b comprises a hinged shelf 20, 22 and one or more flanges 14 are laterally offset therebetween. For example, as depicted, each end 11a, 11b is provided with a hinged shelf, and three flanges 14 are laterally offset between the shelves 20, 22.

As depicted in FIGS. 1-2 and 4, the connector is configured to provide a different syringe type connection at each end 11a, 11b, wherein the hinged shelves 20, 22 may be configured to both hinge or pivot in one direction yet resist pivoting in another direction. The hinged shelves 20, 22 provide for dual functionality, providing for the ability to use the connector 10 to transfer fluids to/from a bottle B with either male orientated oral slip tip syringes or ISO 80369-3 compatible syringes, depending on how the connector was engaged with the bottle B.

Figure 13:
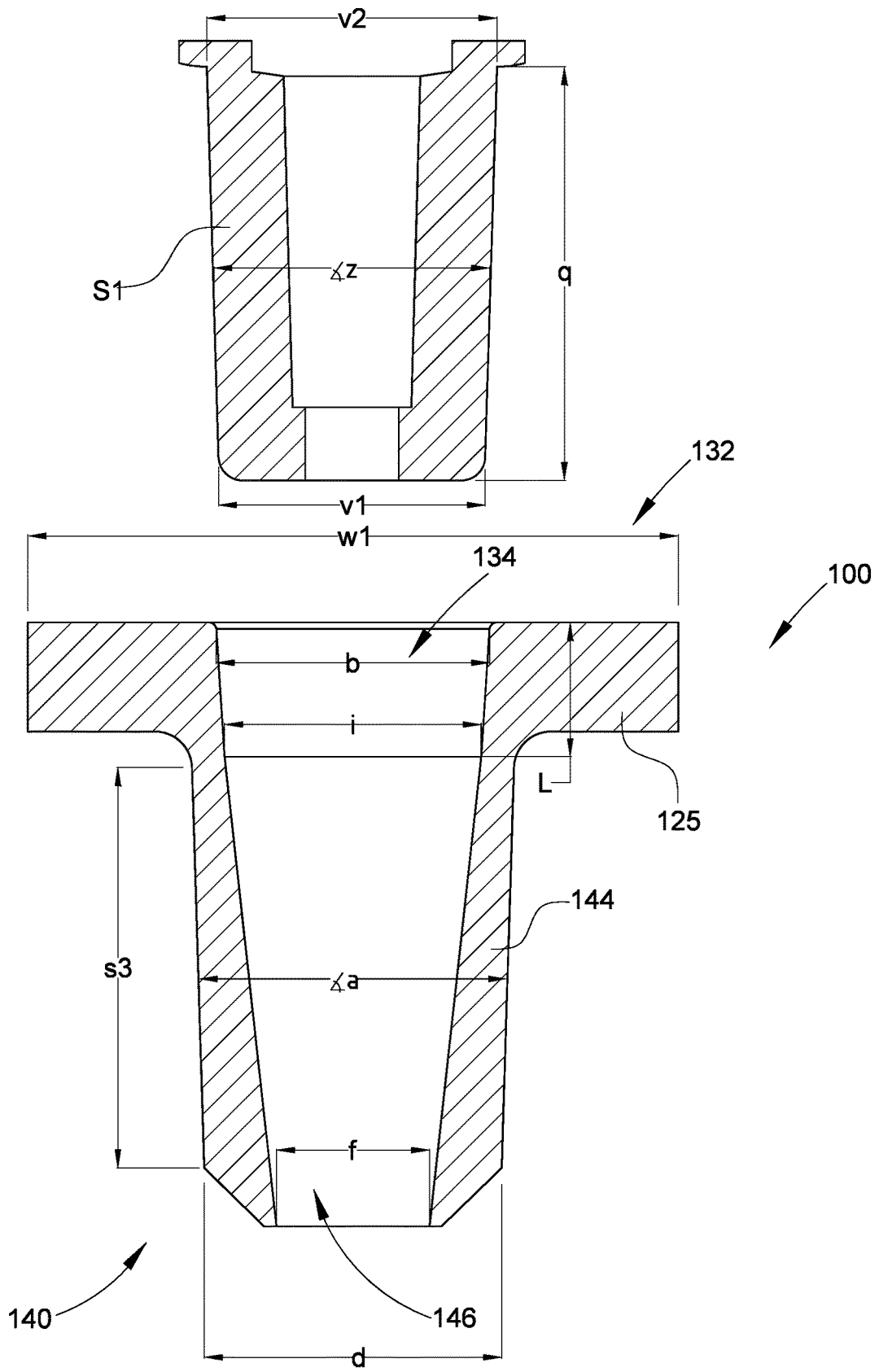
FIG. 13 shows a cross-sectional view of the coupling of FIG. 11, and showing a first syringe positioned near an engageable port thereof.

The first end 11a comprises a female port 32, which is sized and shaped to be configured for sealing engagement with a male oriented slip tip syringe. The port 32 may be supported by a base or floor portion 30 which extends between the cylindrical body 12 and the female port 32. The floor portion 30 is generally planar with the outer surface of the shelf 22. A protrusion or indention can be provided on the floor 30, and generally surrounding the port 32, for example, to act as a sealing surface against an inner surface of a cap to be placed on the bottle B. Optionally, the floor 30 can be at least partially raised or offset relative to the outer surface of the shelf 22, for example, so as to generally act as a lead-in portion and to function as a sealing surface against an interior of the cap. According to example embodiments, the port 32 is preferably dimensioned so as to provide for sealing engagement with a male orientated oral slip tip syringe. FIG. 13 shows example dimensions of a male orientated oral slip tip syringe and corresponding port.

A conduit 34 is defined within the port 32 which fluidly communicates with conduit 46 of a coupling 40 of the second end 11b. The coupling 40 comprises an annular recess 42 defining a male port 44 that comprises the conduit 46 centrally positioned therein and communicating with the conduit 34. Thus, the first end 11a comprises a port 32 configured for sealing engagement with a male orientated oral slip tip syringe and the second end 11b comprises a coupling 40 comprising a male port 44. In some configurations, the male port 44 is configured to accept ISO 80369-3 syringes, sometimes commonly referred to as ENFit™ and ENFit™ Low Dose Tip (LDT) syringes. The male port 44 may take on the slip configuration as shown. Alternatively, the male port 44 may take on a threaded configuration, for example, wherein a collar comprising internal threads is configured for engagement with lugs or ribs formed along an outer portion of an ISO 80369-3 compatible female syringe tip. The male port may extend a sufficient amount so that the opening and conduit 46 thereof may be sealed against a surface on the underside of the bottle cap. According to example embodiments, the cylindrical body 12 comprises an inner diameter D2 of between about 9.0-40.0 millimeters, for example between about 10.0-35.0 millimeters according to one example embodiment. According to another example embodiment, the inner diameter D2 of the cylindrical body 12 is between about 12.0-17.0 millimeters.

For example, as depicted in FIG. 6, the connector 10 is sealingly engaged with the open end of the bottle B in the first configuration and with the port 32 being accessible at the end of the bottle opening, with syringe 51 inserted therein and the cap removed. As the second end 11b is inserted within the opening, the shelf 20 hinges or pivots inwardly about the living hinge 52 and slidingly engages an interior surface of the bottle B. The connector 10 is fully inserted when the stop surface 26 of the shelf contacts an end surface of the opening of the bottle B. As depicted in FIG. 5, a cutout, notch or indention 50 may be formed between the cylindrical body 12 and the shelves 20, 22, for example, to form a living hinge therebetween, thereby allowing the shelves 20, 22 to hinge or pivot inwardly towards the cylindrical body (e.g., inwardly), but to remain substantially transverse relative to the cylindrical body when attempting to hinge or pivot the shelves away from the cylindrical body (e.g., outwardly). For example, a cutout 50 about at or nearby the desired pivot location of the living hinge 52 allows for a desired amount of displacement or pivoting of the shelves 20, 22 relative to the cylindrical body 12. According to example embodiments, the cutout 50 forms a generally V-shaped void that can be sized to provide for a desired amount of pivoting functionality of the shelves relative to the body, for example, to provide enough flexure for being inserted within the bottle B, but while also providing rigidity and the ability to counter forces acting transverse a stop surface that is defined on each of the shelves 20, 22.

Referring to FIGS. 1-2 and 5, the cutout 50 is generally ring-like or annular in shape and outwardly offset from the syringe coupling, for example, defining a ring-like, V-shaped void around the entirety of the ends 11a, 11b of the connector 10 where the cylindrical body 12 intersects with the shelves 20, 22. In example embodiments, the width L3 of the cutout 50 is between about 0.01-3 millimeters, for example about 0.184 millimeters according to one example embodiment. According to another example embodiment, the width L3 of the cutout is about 0.35 millimeters. The V-shaped extension's depth is configured to define a hinge thickness L4 of about 0.20-0.79 millimeters, for example about 0.54 millimeters according to one example embodiment. In example embodiments, the V-shaped cutout supports the one-direction inward pivoting of the shelves 20, 22 towards the cylindrical body 12, yet substantially prevents any outward pivoting thereof away from the cylindrical body 12. For example, the cutout 50 is positioned on outermost surfaces of the ends 11a, 11b, and generally between the shelves 20, 22 and cylindrical body 12, so that a living hinge 52 is formed on interior portions of the shelves 20, 22, thereby facilitating the shelves 20, 22 in allowing for an inward pivot but resisting any outward pivoting thereof.

According to other example embodiments, any other desired sized and shaped cutouts, grooves, recessed reliefs, etc. can be formed with one or more portions of the shelves (or other features of the connector) or outermost ribs near the ends of the connector 10. According to some example embodiments, the cutout could comprise a width at its maximum depth at least equal to its width L3, for example, to provide a more defined hinge of a desired thickness L4. at the outer surfaces of the ends 11a, 11b. such that the connector can be sealingly engaged with the open end of the bottle B in either a first configuration (FIG. 6) or a second configuration (FIG. 7).

FIG. 7 shows the connector 10 engaged with the opening of the bottle B in the second configuration with the first end 11a inserted within the opening. The stop surface 24 of the shelf 20 is engaged with the end of the opening of the bottle B. The ISO80369-3 compatible coupling 40, depicted as a male port 44, is provided for engagement by an ISO 80369-3 compatible syringe S2.

FIGS. 8-9 show a connector 10' according to another example embodiment of the present invention. According to example embodiments, the shelves 20', 22' can be shaped to comprise at least some draft or have some slope or relief provided to the outer surfaces thereof. According to example embodiments, an angle β is defined between the sloped surface and a horizontal plane. In example embodiments, the angle β is between about 5-35 degrees, for example about 14-16 degrees according to one example embodiment. As shown in FIG. 9, the width L3' of the cutout 50' can be substantially small, for example, between about 0.01-0.050 millimeters, for example about 0.028 millimeters according to one example embodiment. In example embodiments, the cutout 50' comprises a large enough width L3 to provide the necessary relief for the hinge 52', to allow for inward pivoting thereof, for example, up to the angle α, which is about 90 degrees according to example embodiments. In some example embodiments, if not integral with the molding process, a second process may be provided to incorporate the cutout 50' at the ends of the connector 10', for example, by forming an annular slit or razor-edge cut to provide at least some separation between the cylindrical body 12' and the shelves 20', 22'.

FIG. 10 shows a connector 10 comprising shelves 20", 22", which are substantially similar to the shelves 20', 22' as described above. According to example embodiments, however, the shelves 20", 22" do not comprise a slit, and thus, the entirety of the shelf 20", 22" acts as a living hinge to provide for inward pivoting but resist outward pivoting by virtue of its scalene right triangle geometry. Preferably, the shelves 20", 22" can be sized and shaped as desired to provide for dual functionality. According to one example embodiment, one or more cutouts can be provided around the periphery of the shelves 20", 22" to facilitate ease of engagement when inserted in the bottle B yet rigidity and sturdiness when acting as a stop surface when oriented in an opposite manner.

Figure 12:
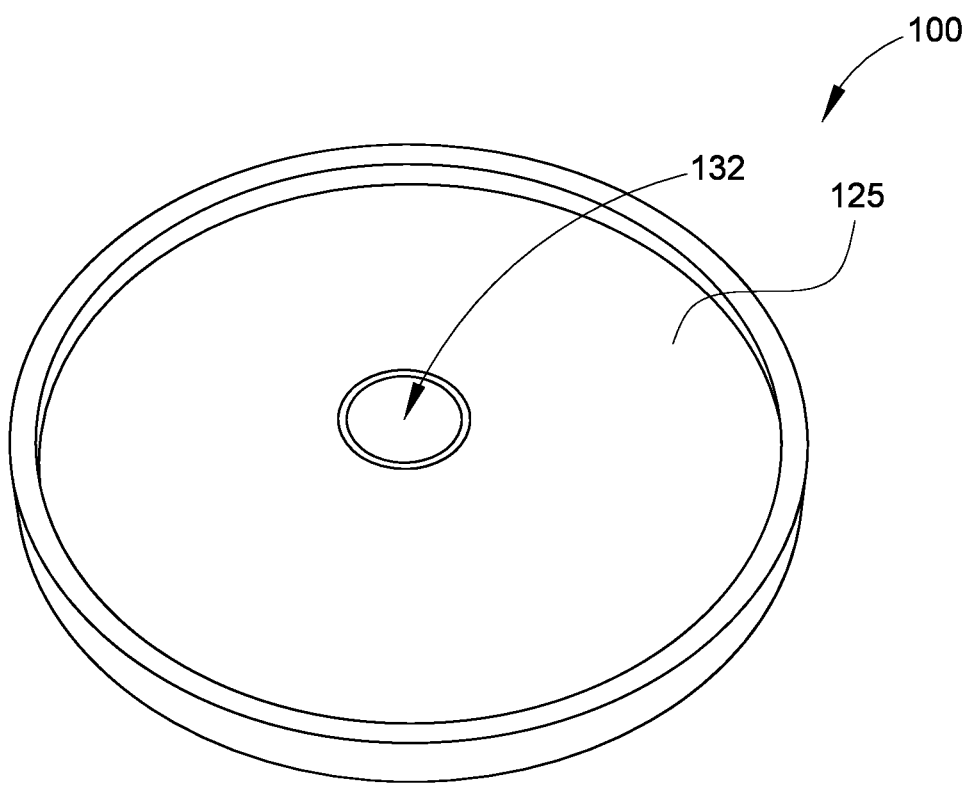
FIG. 12 shows a second perspective view of the coupling of FIG. 11.

FIGS. 11-14 depict a connector 100 that allows for access with both a male oral slip tip syringe and an ISO 80369-3 syringe, through different connection points and sealing surfaces, located on opposite sides of the same coupler. FIG. 11 depicts a first end of the connector 100 comprising an ISO 80369-3 compatible male port 144 that is centrally-positioned within a flange 125 outwardly extending therefrom and configured for engagement with a ISO 80369-3 compatible female tip syringe, forming a seal capable of fluid transfer, between the outside of the port and the inside of the syringe tip. FIG. 12 depicts the second end of the connector 100 wherein a female port 132 is provided and configured for engagement with a male oral slip tip syringe, forming a seal capable of fluid transfer, between the outside surface of the male syringe tip and the inside surface of the female port 132.

Figure 14:
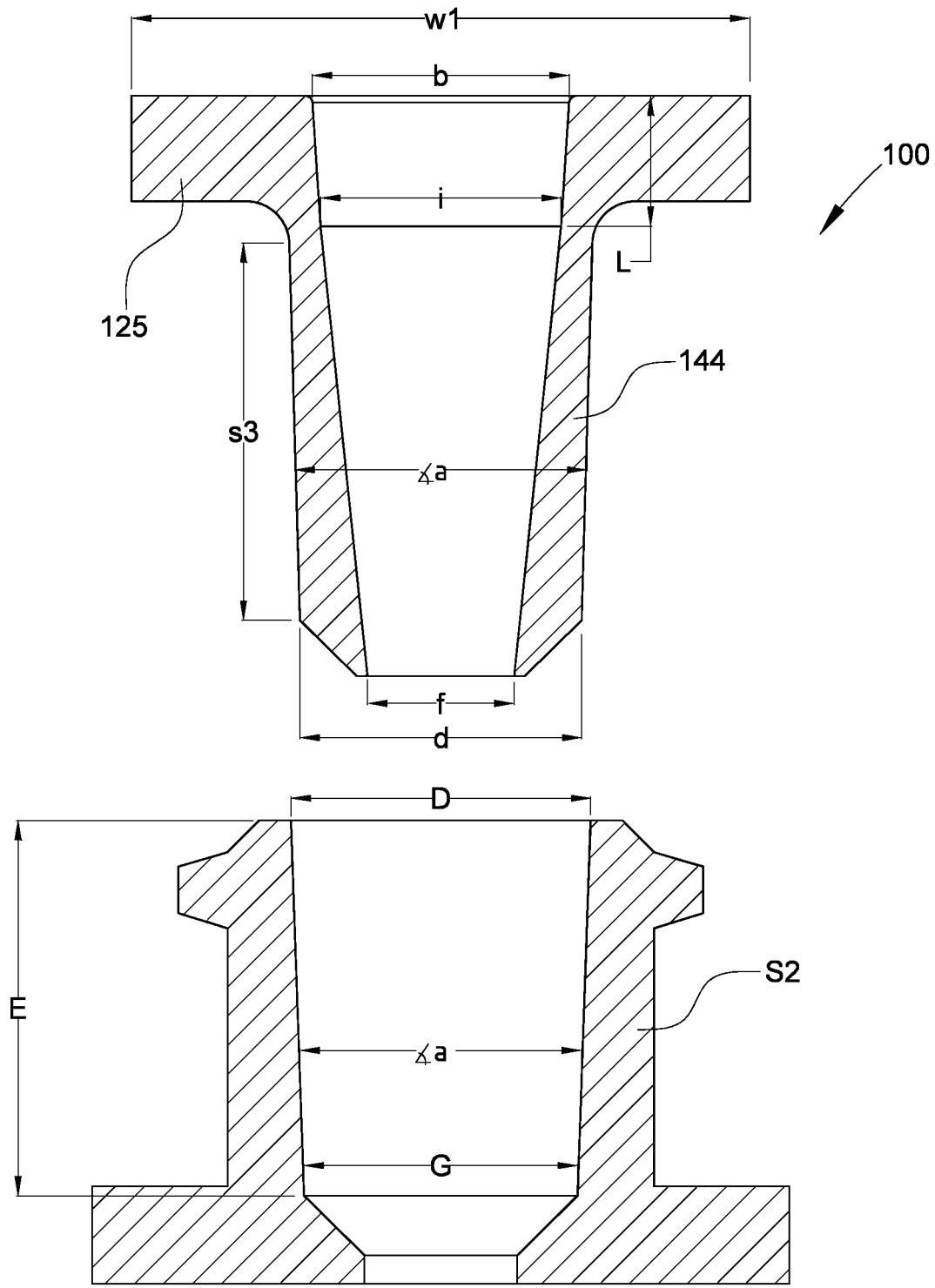
FIG. 14 shows a cross-sectional view of the coupling of FIG. 11, and showing a second syringe positioned near an engageable port thereof.

FIG. 13 shows a cross sectional view of a male oral slip tip syringe S1 on top, aligned for connection with the female port 132 of the connector 100 at the bottom of the figure. FIG. 14 shows a cross sectional view of an ISO 80369-3 female tip syringe S2 on the bottom, aligned for connection with the male port 144 of the connector 100 at the top of the figure. The connector 100 and referenced syringe tips shown in FIGS. 13-14 are typically circular when viewed from overhead. The referenced dimensions in FIGS. 13-14 are listed in Table 1. These dimensions demonstrate the interferences needed to form a seal between the male and female ports of the technology and their corresponding (oppositely orientated) syringe tips (male oral slip tip syringes and the ISO 80369-3 female tip syringes). The dimensions shown in Table 1 are meant to quantify an ideal working range for the syringes and the ports of the technology, but actual parts, typically injection molded, may deviate outside these ranges. Table 1 values expressed as a dash, "-", represent boundless values.

TABLE 1

Dual Port Coupler

| | | Dimensions (mm) | | |
|---|---|---|---|---|
| Reference | Designation | Minimal | Nominal | Maximum |
| a | Angle of taper | — | 3.44° | — |
| a1 | Outside taper of dual port | 1.00° | 2.00° | 3.44° |
| b | Inside diameter at top of port | 4.80 | 4.85 | 4.90 |
| d | Outside of diameter at tip of male taper | 5.36 | 5.41 | 5.46 |
| D | Inside diameter of female connector | 5.64 | 5.69 | 5.74 |
| E | Depth of female connector | 7.04 | 7.14 | 7.24 |
| f | Inside of diameter at tip of male taper | 0.00 | 2.90 | 2.95 |
| G | Inside diameter of the female connector at E | 5.21 | 5.26 | 5.31 |
| g1 | Outside diameter at top of dual port | 5.55 | 5.60 | 5.64 |
| g2 | Outside diameter at bottom of dual port | 5.71 | 5.86 | 5.91 |
| g3 | Outside diameter at top of raised female port | 4.80 | 7.00 | — |
| i | Inside diameter at bottom of female port | 4.30 | 4.60 | 4.65 |
| k | Inside diameter at bottom of dual port | 4.30 | 4.60 | 4.65 |
| l | Depth of female port | 1.25 | 2.50 | 7.50 |
| q | Height of syringe nozzle | 7.11 | 7.36 | 7.61 |
| s1 | Height of dual port | 3.00 | 5.50 | 8.00 |
| s2 | Height of raised female port | 1.25 | 6.00 | 7.50 |
| s3 | Height of male nozzle | 6.82 | 7.00 | — |
| v1 | Outside diameter of syringe nozzle at tip | 4.70 | 4.80 | 4.90 |
| v2 | Outside diameter of syringe nozzle at q | 5.10 | 5.20 | 5.30 |
| w1 | Outside diameter | 4.80 | 13.30 | — |
| w2 | Outside diameter | 5.71 | 13.30 | — |
| x | Inside taper of raised female port | 1.00° | 2.00° | 6.00° |
| y | Inside taper of dual port | 1.00° | 2.00° | 6.00° |
| z | Outside taper of syringe nozzle | 2.26° | 2.76° | 3.26° |

Figure 15:
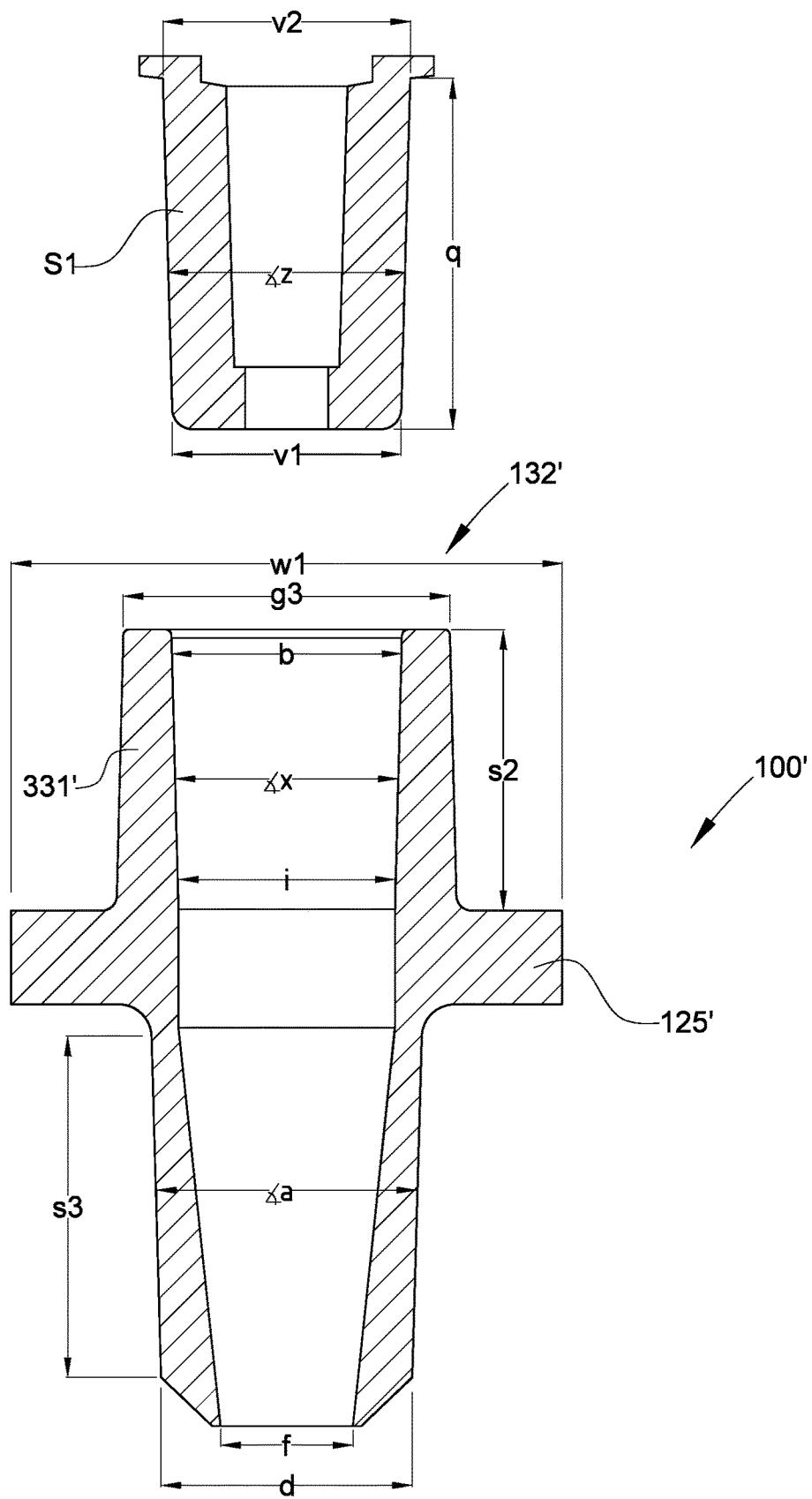
FIG. 15 shows a cross-sectional view of a coupling according to another example embodiment of the present invention, and showing a first syringe positioned near an engageable port thereof.

FIG. 15 shows a connector 100' according to another example embodiment of the present invention. In example embodiments, the connector 100' allows for sealing engagement with both a male oral slip tip syringe and an ISO 80369-3 syringe, through different connection points and sealing surfaces, located on opposite sides of the same connector. In example embodiments, the connector 100' is generally similar to the connector 100 as described above, however, according to some example embodiments the female port can be extended a length s2 from a surface of the flange 125'. In example embodiments, an extruded post 331' extends the length s2, and defines the female port 132' within the post 331'. The referenced dimensions in FIG. 15 are listed in Table 1. These dimensions demonstrate the interferences needed to form a seal between the male and female ports of the technology and their corresponding (oppositely orientated) syringe tips (male oral slip tip syringes and the ISO 80369-3 female tip syringes). The dimensions shown in Table 1 are meant to quantify an ideal working range for the syringes and the ports of the technology, but actual parts, typically injection molded, may deviate outside these ranges. Table 1 values expressed as a dash, "-", represent boundless values.

According to example embodiments, the connectors as described throughout FIGS. 1-15 may be utilized for direct fluid transfer between different syringe types, for example, ISO 80369-3 compliant syringes and male oral slip tip syringes by simultaneously coupling the appropriate formatted syringe at the ends thereof. Accordingly, in addition to the connectors providing for coupling engagement with one or more components such as a bottle or a single port of a syringe type, the connectors can similarly act as a syringe-to-syringe fluid transfer connector.

Figure 16:
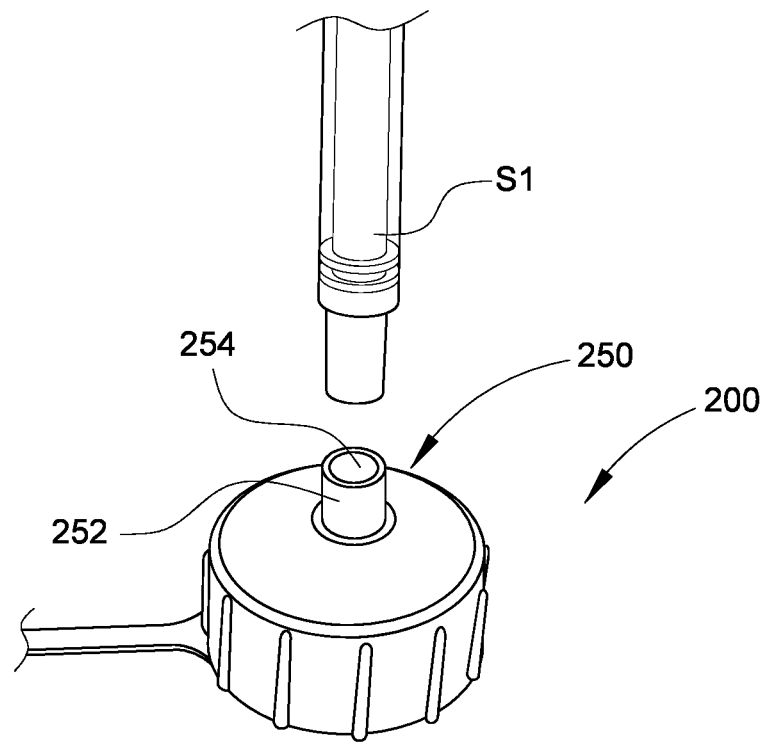
FIG. 16 shows a perspective view of a coupling having a male post according to another example embodiment of the present invention, and showing a first syringe positioned nearby the male post for connection therewith.
Figure 17:
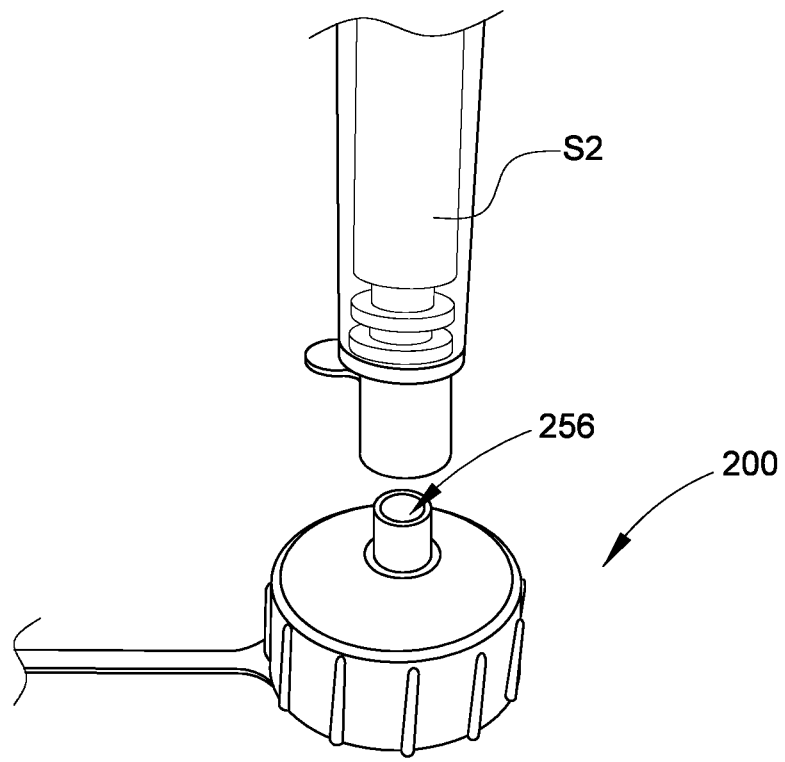
FIG. 17 shows a perspective view of the coupling of FIG. 16, showing a second syringe positioned nearby the male post for connection therewith.
Figure 18:
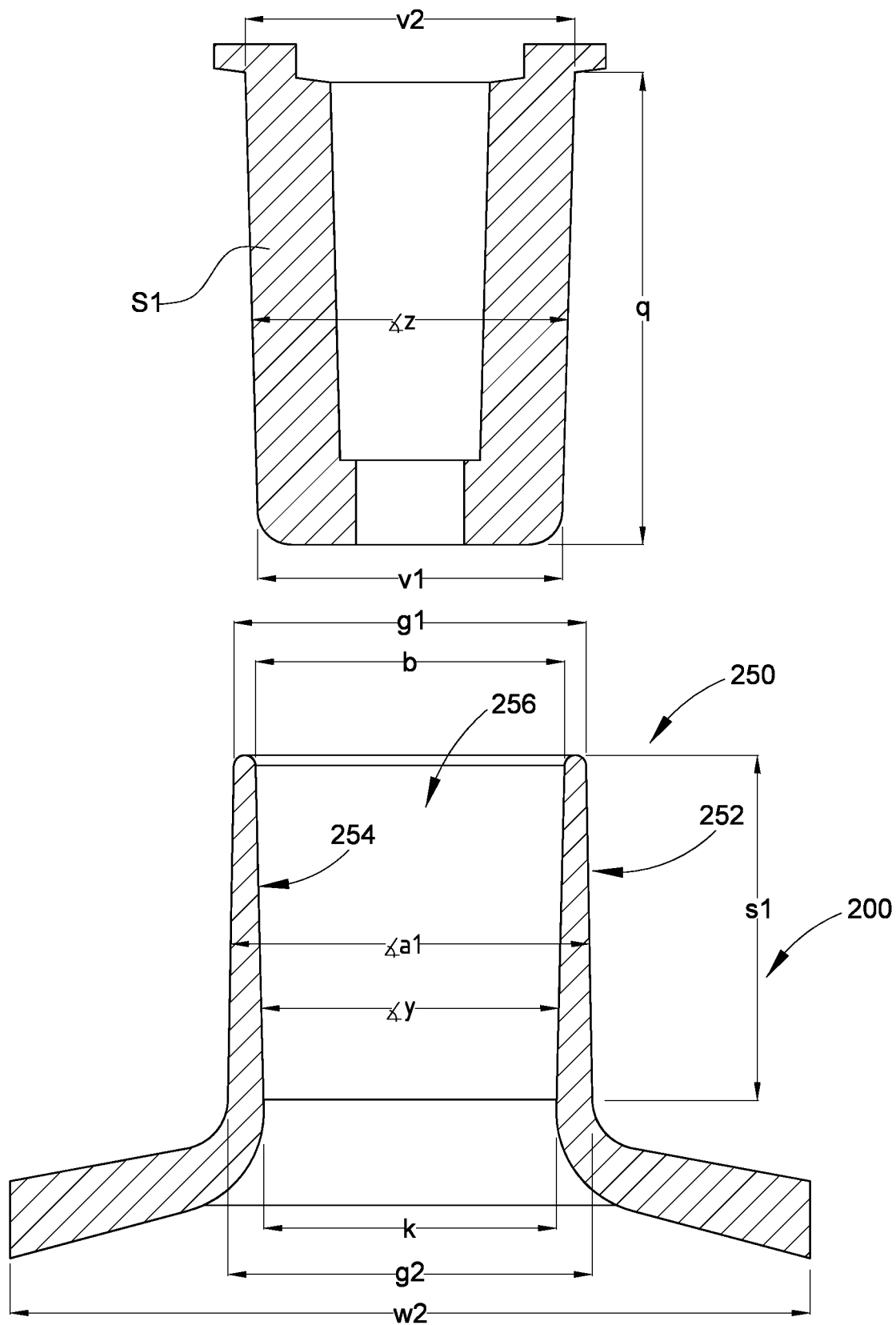
FIG. 18 shows a cross-sectional view of FIG. 16.

FIGS. 16-19 show a connector 200 according to another example embodiment of the present invention. As depicted, the connector 200 is generally in the form of a bottle cap comprising an internal threaded portion for engagement with the outer threads of a bottle B, and a tethered end cap for closure of a conduit formed by a universal or dual connector port 250, which is sized and shaped to provide for sealing engagement with both a male orientated slip tip syringe and an ISO 80369-3 female tip syringe. In example embodiments, the connector 250 comprises an outer surface 252, an inner surface 254, and a conduit 256 extending therethrough. As depicted in FIGS. 16 & 18, the male orientated slip tip syringe 51 is sealingly engageable by its outer surface sealingly engaging with the interior surface 254 of the connector 250. Similarly, in FIGS. 17 & 19, the female syringe tip of the ISO 80369-3 compatible syringe S2 is sealingly engageable by its inner surface sealingly engaging with the outer surface 252 of the connector 250. According to example embodiments, the connector 250 is beneficial to users because it allows for them to use both male oral slip tip syringes and ISO 80369-3 female tip syringes, on the same medicine bottle, without having to switch to a different adaptor that is only compatible with their syringe type. The referenced dimensions in FIGS. 18-19 are listed in Table 1. These dimensions demonstrate the interferences needed to form a seal between the dual port technology and both the male oral slip tip syringe and the ISO 80369-3 female tip syringe. The dimensions shown in Table 1 are meant to quantify an ideal working range for the syringes and the dual port technology, but actual parts, typically injection molded, may deviate outside these ranges. Table 1 values expressed as a dash, "-", represent boundless values.

According to additional example embodiments, the connector 250 may be applied to other connectors, for example, a "press-in" bottle adaptor, or for example, other desired connectors common among fluid transfer. According to one example embodiment, the connector 250 may be utilized in place of the connector 44 shown in FIGS. 2, 4, 6-8 and 10.

Figure 20:
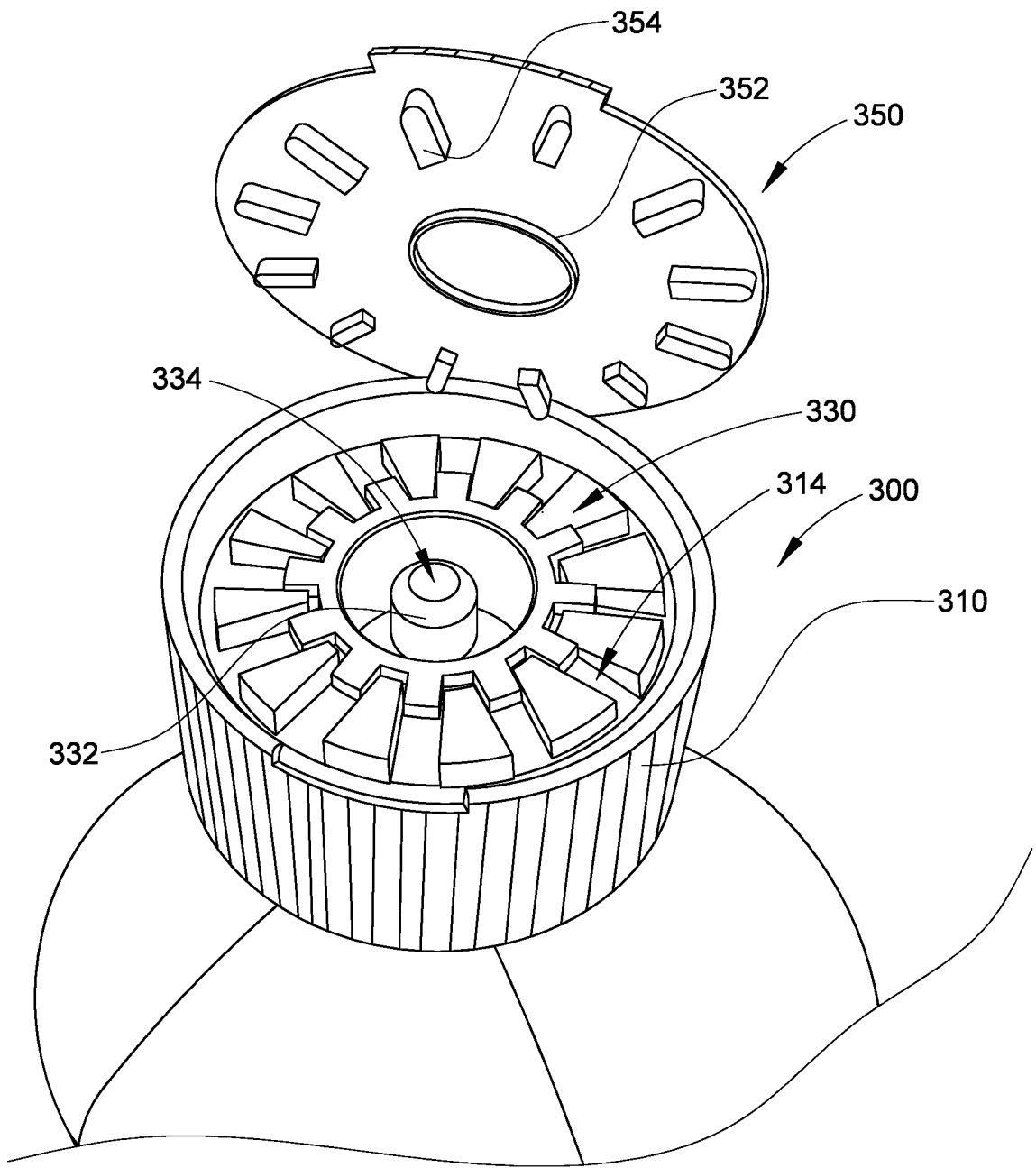
FIG. 20 shows perspective view of a coupling according to another example embodiment of the present invention, and showing an end of a bottle connected therewith.
Figure 21:
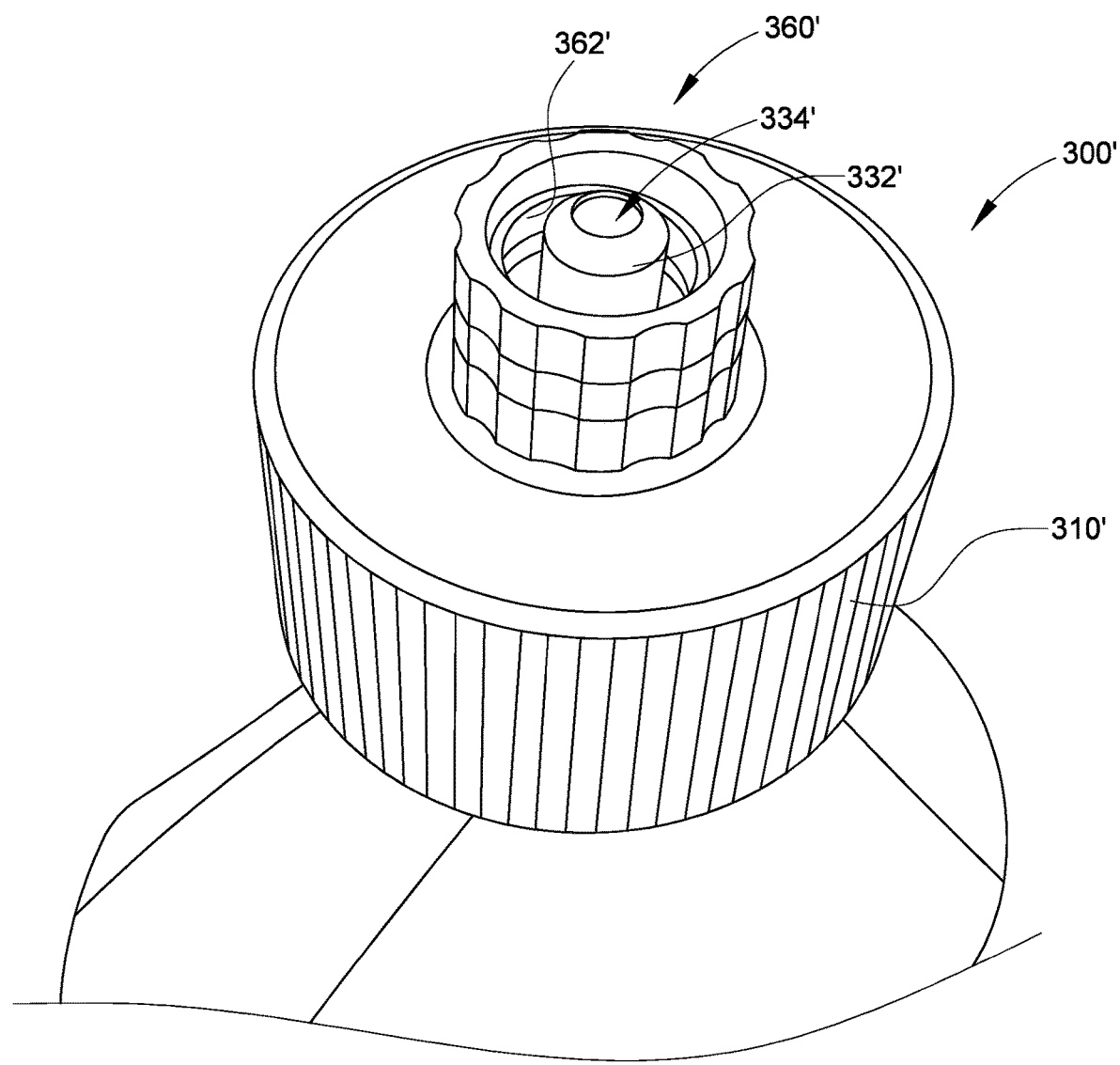
FIG. 21 shows a perspective view of a coupling according to another example embodiment of the present invention, and showing an end of a bottle connected therewith.
Figure 22:
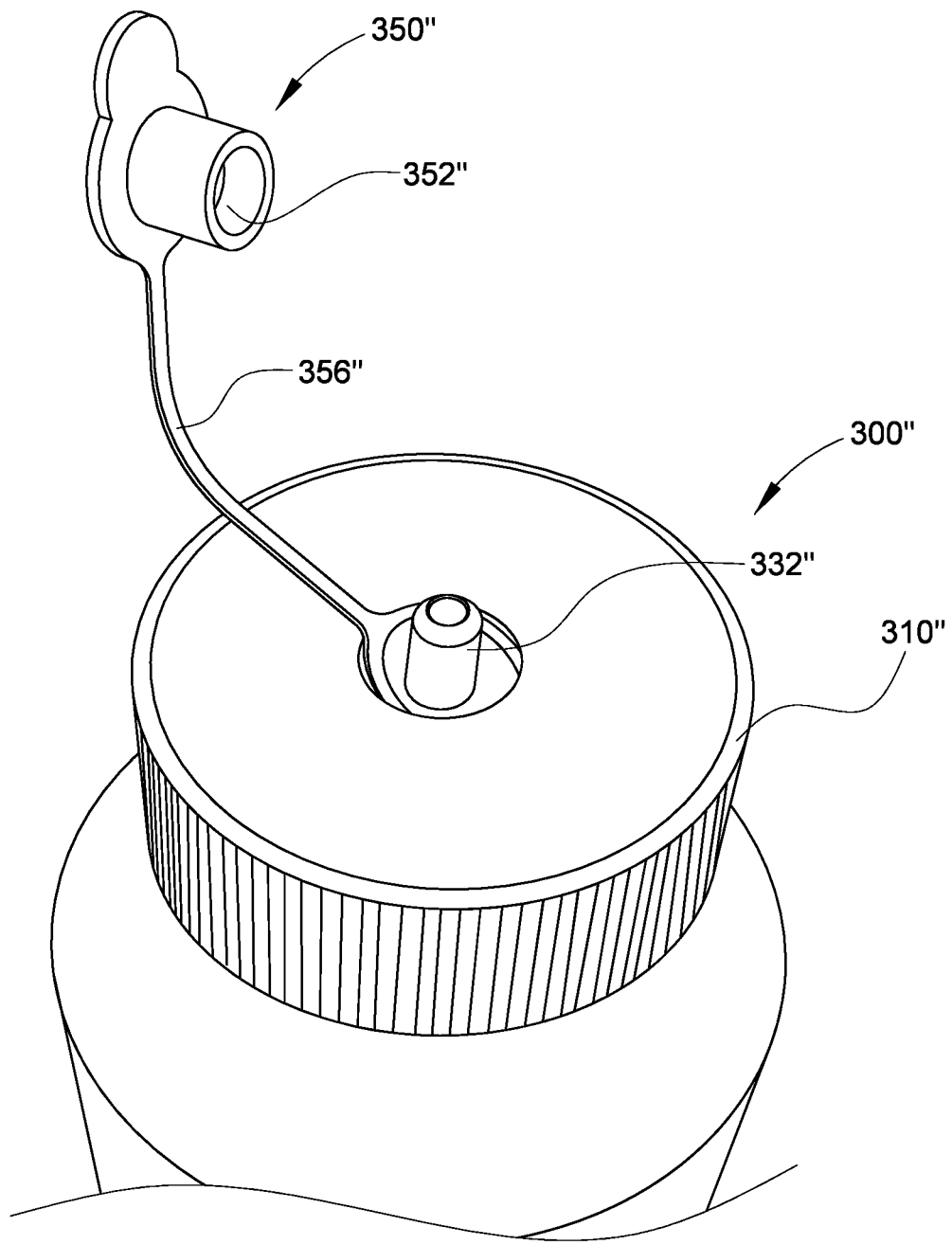
FIG. 22 shows a perspective view of a coupling according to another example embodiment of the present invention, and showing an end of a bottle connected therewith.

FIGS. 20-23 show a plurality of connectors incorporated with typical screw-on child-resistant caps for medicine bottles. FIG. 20 shows a connector 300 comprising a hinged lid 352 with the port access located under the hinged section. The male port 332 of an ISO 80369-3 compatible connector is attached to the threaded section of the cap 310 that engages with the medicine bottle's threads. The outer portion of the cap rotates independently from the inner threaded section, except when the cap is screwed onto the bottle or when downward pressure is applied to the cap while unscrewing from the bottle. Although the cap lid 352 is hinged, when closed the teeth 354 on the hinged section still engage with the splines 314 on the threaded section, allowing the child resistant feature to function as expected. In some configurations, the male port 332 is configured to accept ISO 80369-3 syringes. The male port may take on the slip configuration shown. Alternatively, the male port may take on a threaded configuration. The opening 334 of the male port 332 may be sealed against a bump on the underside of the hinged lid 352 so that fluids do not leak from the port. Alternatively, the male port 332 may be sealed with a membrane seal or a valve. In other example embodiments, the male port 332 may be sealed with its own cap or plug and those may or may not be tethered to the threaded component of the assembly and they would still allow for functionality of the hinged lid and the child resistant feature of the cap. For example, FIG. 22 shows a tethered plug 350" of a connector 300" comprising a plug 352" and a tether 356" connected thereto, which can provide for sealing engagement with the male port 332", for example to seal the opening or conduit thereof.

FIG. 21 shows a connector 300' comprising a coupling 360' comprising a male port 332' defining a conduit 334' passing therethrough and an outwardly offset and internally threaded collar 362'. port that is positioned above the plane of the outer section of the child resistant cap. In example embodiments, the male port 332' is of male orientation and allows access for a female oriented syringe. However, these orientations could be reversed. In this embodiment, the coupling 360' is integrated with the threaded section of the cap that engages with the medicine bottle's threads. The outer portion of the cap rotates independently from the inner threaded section, except when the cap is screwed onto the bottle or when downward pressure is applied to the cap while unscrewing from the bottle. Some configurations of this embodiment may feature smooth surfaces along the exterior of the port and or port housing so that it is more difficult to grip this section so that the child resistance feature of the cap is maximized. In example embodiments, the coupling 360' is a threaded male port that follows ISO 80369-3 (ENFit and ENFit LDT). Alternatively, this male port may feature a slip (non-threaded) configuration. In other configurations this male port may accept other female syringe types. In another embodiment, the port 332' is female and the syringe is male. In example embodiments, the section of the port that is above the plane of the cap may act as a reservoir to aid in funneling all the fluids from the bottle when in the inverted/filling position. Closures for sealing the opening 334' of the coupling 360' can be in the form of threaded closures, which may or may not be tethered to the port component. The closure may feature a threaded or a slip fit engagement. Alternatively, the port 332' may be sealed with a plug that goes into the opening of the male feature and this plug may or may not be tethered to the port. In example embodiments, the port 332' stands above the plane of the cap 310'. The port 332' passes through the cap so that the cap 310' can still rotate/operate for the child resistant functionality. In example embodiments, the port 332' is part of the threaded component of the cap 310' while the outer housing is a separate component of the assembly. In example embodiments, the port 332' may be an integral portion of the threaded component of the cap. Optionally, the port 332' is separate and assembled with the threaded component.

Figure 23:
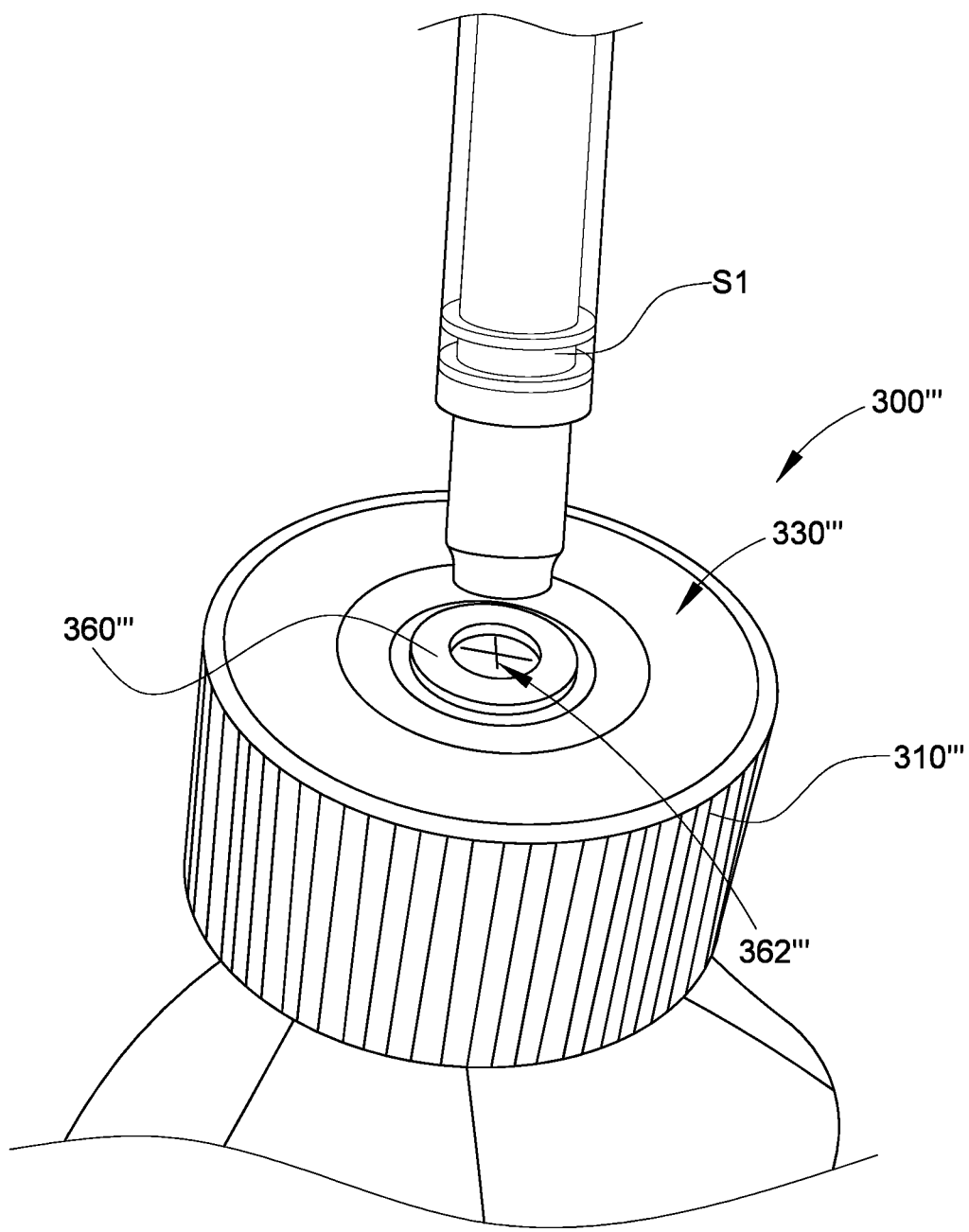
FIG. 23 shows a perspective view of a coupling according to another example embodiment of the present invention, and showing an end of a bottle connected therewith and a first syringe positioned nearby a port thereof.

FIG. 23 shows a connector 300'" comprising a port 330'" for syringe access that is flush or nearly flush with the top outer surface of the child resistant cap. In example embodiments, the port 330'" (slightly recessed below the membrane 360'") is of the female orientation and allows access for a male oriented syringe, for example a male orientated oral slip tip syringe S1 according to example embodiments. However, these orientations could be reversed, for example, wherein the port is of male orientation configured for engagement with a female oriented syringe tip. In example embodiments, the port is attached to the threaded section of the cap that engages with the medicine bottle's threads but is engaged with the outer portion of the cap in such a way that the outer portion of the cap rotates independently from the inner threaded section, except when the cap is screwed onto the bottle or when downward pressure is applied to the cap while unscrewing from the bottle. In example embodiments, the port 330'" has a membrane 360'" comprising a resealable "x" slit or cut that allows for the syringe to be inserted and is self-sealing when the syringe is not in place. Alternatively, this port may be configured as an open design that utilizes a plug to seal the port. In some configurations this plug may be hinged to the cap or tethered to the cap. In example embodiments, the female port as described with respect to FIG. 23 is configured to generally accept oral/enteral male tipped syringes of all volume capacities.

According to additional example embodiments, the connectors of FIGS. 20-23 may also be configured to accept male slip tip syringes, or for example, may be configured for accepting at least two different syringe types, for example, such as similarly described regarding the male post of FIGS. 16-19. Preferably, regardless of the syringe types connectable with the connectors, the access port is incorporated in the child resistant cap wile the cap's child-resistant functionality thereof remains the same.

According to another example embodiment, the connector comprising a coupling that's comprised of softer/more deformable materials, for example, to allow for sealingly engaging with both female and male tip syringes. According to example embodiments, the coupling may be deformable and invertible. According to one example embodiment, the coupling may flex and deform to establish its connection with a male oral slip tip syringe. As the syringe is pressed into the male port, it deforms to the point that it becomes inverted. Accordingly, what was the male exterior surface of the coupling then essentially becomes a female surface, which seals against the male oral slip tip syringe. According to example embodiments, the coupling does not necessarily deform, other than a slight compression for a sealing fitment, when the tip of the ISO 80369-3 compatible syringe surrounds and connects with the male port of the coupling.

According to example embodiments, FIGS. 1-23 represent embodiments that, in actual use, may include closure mechanisms and or sealing mechanisms to seal the contents of the medicine bottles, particularly during storage.

What is claimed is:

1. A fluid transfer adaptor comprising a male port comprising a conduit extending therethrough, the male port supported by a base portion extending between an outer attachment body and the male port, wherein the male port is configured for connection with an ISO 80369-3 compliant female tip syringe, at least a portion of an outer periphery of the male port providing for sealing engagement with the ISO 80369-3 compliant female tip syringe, and wherein at least a portion or extension of the male port's interior providing for sealing engagement with at least a portion of an outer peripheral surface of a male oriented oral slip tip syringe.

2. The fluid transfer adaptor of claim 1, wherein the male port comprises a base end attached to the base portion and a free end extending from the base end, wherein the outer diameter of the free end is between about 5.55-5.64 millimeters, and wherein the inner diameter of the free end is between about 4.80-4.90 millimeters.

3. The fluid transfer adaptor of claim 1, wherein the outer attachment body comprises a cylindrical body configured for attachment to an opening of a bottle.

4. The fluid transfer adaptor of claim 3, wherein the cylindrical body comprises an outer peripheral surface defining a plurality of flanges, the flanges configured for sealing engagement within the opening of the bottle.

5. The fluid transfer adaptor of claim 4, further comprising a hinged shelf at each end of the cylindrical body, wherein a living hinge is formed between each hinged shelf and the cylindrical body, wherein each hinged shelf is configured to permit inward pivoting thereof towards the cylindrical body yet resist pivoting thereof in an opposite direction away from the cylindrical body.

6. The fluid transfer adaptor of claim 5, wherein a first end of the adaptor comprises a first hinged shelf and a first coupling and a second end of the adaptor comprises a second hinged shelf and a second coupling, wherein when the second coupling is to be used for fluid transfer, the first hinged shelf is configured to pivot inwardly towards the cylindrical body and the second hinged shelf is configured for acting as a stop against an end of an opening of the bottle, and wherein when the first coupling is to be used for fluid transfer, the second hinged shelf is configured to pivot inwardly towards the cylindrical body and the first hinged shelf is configured for acting as a stop against the end of the opening of the bottle, and wherein the hinged shelf of each end of the connector is configured for dual functionality.

7. The fluid transfer adaptor of claim 6, wherein the first coupling comprises the male port and the second coupling comprises a female port.

8. The fluid transfer adaptor of claim 1, wherein the base portion comprises a first side and a second side, the first side comprising the male port extending therefrom and the second side comprising a female port that is aligned and fluidly connected with the conduit of the male port extending from the first side of the base portion, wherein the female port is configured for connection with a male oriented oral slip tip syringe.

9. A fluid transfer connector for the transfer of fluids to and/or from at least one syringe, the connector comprising a conduit extending between first and second ends, the first end comprising a male port and the second end comprising a female port, the ports connected to a base portion outwardly extending therefrom such that a first side of the base portion comprises the male port and a second side of the base portion comprises the female port, wherein the male port is configured for connection with an ISO 80369-3 compliant female tip syringe and wherein the female port is configured for connection with a male orientated oral slip tip syringe.

10. The fluid transfer connector of claim 9, wherein the female port is outwardly offset from a second side of the base portion.

11. The fluid transfer connector of claim 9, wherein the base portion comprises a flange-like member outwardly extending from the ports.

12. The fluid transfer connector of claim 9, further a comprising cylindrical body connected to the base portion and configured for attachment within an opening of a bottle, the cylindrical body comprising an outer peripheral surface defining at least one flange configured for sealing engagement within the opening of the bottle, the cylindrical body further comprising a hinged shelf at each end thereof, wherein each hinged shelf is configured to permit inward pivoting thereof towards the cylindrical body yet resist pivoting thereof in an opposite direction away from the cylindrical body.

13. The fluid transfer connector of claim 12, further comprising a slit formed between the cylindrical body and the hinged shelves to permit the inward pivoting thereof towards the cylindrical body.

14. The fluid transfer connector of claim 12, wherein the hinged shelves are shaped to resist outward pivoting by virtue of their scalene right triangle geometry.

15. The fluid transfer connector of claim 12, wherein the hinged shelf is configured for dual functionality, acting as both a stop oriented in a first direction and a sealing flange in a second direction.

16. A fluid transfer adaptor comprising a male port comprising a conduit extending therethrough, the male port supported by a base portion outwardly extending therefrom, wherein at least a portion of the outer peripheral surface of the male port is configured for sealing engagement with at least a portion of an ISO 80369-3 compliant female tip syringe, and wherein the male port's interior or an extension thereof, both of which are in fluid communication with the conduit, is configured for sealing engagement with at least a portion of a male oriented oral slip tip syringe.

17. The fluid transfer adaptor of claim 16, wherein the male port comprises a base end attached to the base portion and a free end extending from the base end, wherein the outer diameter of the free end is between about 5.55-5.64 millimeters, and wherein the inner diameter of the free end is between about 4.80-4.90 millimeters.

18. The fluid transfer adaptor of claim 17, wherein at least a portion of an inner peripheral surface defined at the inner diameter of the male port's free end is configured for sealing engagement with at least a portion of an outer periphery of a male oriented oral slip tip syringe.

19. The fluid transfer adaptor of claim 16, wherein the base portion comprises a first side and a second side, the first side comprising the male port extending therefrom and the second side comprising a female port that is aligned and fluidly connected with the conduit of the male port extending from the first side of the base portion, wherein the female port is configured for connection with at least a portion of the outer peripheral surface of the male oriented oral slip tip syringe.

20. The fluid transfer connector of claim 16, further comprising a cylindrical body connected to the base portion and configured for attachment within an opening of a bottle, the cylindrical body comprising an outer peripheral surface defining at least one flange configured for sealing engagement within the opening of the bottle, the cylindrical body further comprising a hinged shelf at each end thereof, wherein each hinged shelf is configured to permit inward pivoting thereof towards the cylindrical body yet resist pivoting thereof in an opposite direction away from the cylindrical body.

* * * * *